(12) United States Patent
Esau et al.

(10) Patent No.: US 7,998,677 B2
(45) Date of Patent: Aug. 16, 2011

(54) MICRORNA DETECTION

(75) Inventors: Christine Esau, La Jolla, CA (US); Scott E. Davis, Oceanside, CA (US); Frank C. Bennett, Carlsbad, CA (US)

(73) Assignee: Regulus Therapeutics, Inc., San Diego, CA (US)

( * ) Notice: Subject to any disclaimer, the term of this patent is extended or adjusted under 35 U.S.C. 154(b) by 15 days.

(21) Appl. No.: 12/393,523

(22) Filed: Feb. 26, 2009

(65) Prior Publication Data

US 2009/0236225 A1   Sep. 24, 2009

Related U.S. Application Data

(60) Provisional application No. 61/031,688, filed on Feb. 26, 2008.

(51) Int. Cl.
*C12Q 1/68* (2006.01)
(52) U.S. Cl. ......................................................... 435/6
(58) Field of Classification Search ...................... 435/6
See application file for complete search history.

(56) References Cited

U.S. PATENT DOCUMENTS

| | | | | |
|---|---|---|---|---|
| 6,664,045 | B1 * | 12/2003 | Hyldig-Nielsen et al. | 435/6 |
| 2006/0189557 | A1 * | 8/2006 | Slack et al. | 514/44 |
| 2006/0199233 | A1 * | 9/2006 | Dahlberg et al. | 435/7.23 |
| 2006/0211024 | A1 * | 9/2006 | Corn et al. | 435/6 |
| 2007/0003939 | A1 * | 1/2007 | Wang et al. | 435/6 |
| 2008/0160511 | A1 * | 7/2008 | Dawson et al. | 435/6 |
| 2008/0269123 | A1 * | 10/2008 | Li et al. | 514/12 |
| 2009/0099034 | A1 * | 4/2009 | Ahlquist et al. | 506/9 |
| 2009/0136949 | A1 * | 5/2009 | Raponi et al. | 435/6 |

FOREIGN PATENT DOCUMENTS

DE    102004026494 A1 * 12/2005

OTHER PUBLICATIONS

Uhlmann E. Biol Chem 1998 379:1045-52.*
English machine translation of DE 102004026494 translated on Aug, 6, 2010, pp. 1-9.*

* cited by examiner

*Primary Examiner* — Brian Whiteman
(74) *Attorney, Agent, or Firm* — Andrus, Sceales, Starke & Sawall, LLP (57) ABSTRACT

Provided herein are methods for detection of miRNA in a sample. In certain embodiments, the sample comprises RNA and is derived from a cell or tissue. The methods of detection employ a competitor molecule to allow for detection of an miRNA in the presence of an anti-miRNA oligonucleotide.

16 Claims, 5 Drawing Sheets

MICRORNA DETECTION

CROSS-REFERENCE TO RELATED APPLICATIONS

This application claims priority to U.S. provisional Ser. No. 61/031,688 filed Feb. 26, 2008, which is incorporated herein by reference in its entirety.

FIELD OF THE INVENTION

Provided herein are methods for detection of miRNA in a sample. In certain embodiments, the sample comprises RNA and is derived from a cell or tissue.

BACKGROUND OF THE INVENTION

MicroRNAs (miRNAs) are a class of small noncoding RNAs that negatively regulate their mRNA targets by binding with imperfect complementarity in the 3'-untranslated region. Largely unrecognized before 2001, it is now clear that miRNA represent a widely conserved mechanism of post-transcriptional gene regulation. In mammals, regulatory roles have been identified for miRNA in many areas of biology, pointing to miRNA as an exciting new class of therapeutic targets with broad applications.

Much information about miRNA function to date has been obtained through inhibition of their function with anti-miRNA oligonucleotides. As miRNAs are short (18-24 nucleotides) nucleic acids, anti-miRNA oligonucleotides targeting miRNAs using Watson-Crick basepairing is a way to achieve specific pharmacological inhibition of miRNA function.

BRIEF DESCRIPTION OF DRAWINGS

FIG. 2. Interference of miRNA detection in presence of anti-miRNA ASOs. The indicated amount of ASO was added into Trizol lysates containing 50 mg liver tissue before RNA purification. PS=phosphorothioate backbone. PO=unmodified phosphate backbone. (a) Northern blotting for miR-122 after separation of RNA on polyacrylamide gel containing 8M urea. (b) Northern blotting for miR-122 after separation of RNA on polyacrylamide gel containing 8M urea and 20% formamide. (c) Real-time RT-PCR detection of miR-122 with TaqMan MicroRNA Assay.

SUMMARY

Provided herein are methods for measuring small RNA levels in a biological sample. In certain embodiments, the small RNA is a small non-coding RNA. In certain embodiments, the small non-coding RNA is a miRNA.

In certain embodiments, a test sample is prepared from a biological sample. In certain embodiments, the test sample comprises RNA isolated from a biological sample. In certain embodiments, the biological sample is derived from cells. In certain embodiments, the cells are isolated from an animal. In certain embodiments, the biological sample is derived from a tissue. In certain embodiments, the biological sample is derived from a cell-free system. In certain embodiments, the biological sample is derived from cells contacted with an anti-miRNA oligonucleotide. In certain embodiments, the biological sample is derived from tissues contacted with an anti-miRNA olignucleotide. In certain embodiments, the contacting occurs in vitro. In certain embodiments, the contacting occurs in vivo.

In certain embodiments, the method comprise contacting a cell with an anti-miRNA oligonucleotide, isolating RNA from the cell to form a biological sample, preparing a test sample comprising the biological sample, adding at least one competitor molecule to the test sample, and detecting free miRNA in the test sample, thereby detecting the miRNA amount in the biological sample.

In certain embodiments, at least one competitor molecule is added to the test sample. In certain embodiments, the competitor molecule comprises an oligomeric compound. In certain embodiments, the oligomeric compound has a nucleobase sequence complementary to the nucleobase sequence of the anti-miRNA oligonucleotide. In certain embodiments, the oligomeric compound is linked to a conjugate at one terminus. In certain embodiments, the conjugate is at the 5' terminus. In certain embodiments, the conjugate is at the 3' terminus. In certain embodiments, the oligomeric compound comprises a conjugate at each terminus. In certain embodiments, the conjugate is a solubility enhancing molecule. In certain embodiments, the solubility enhancing molecule is a surfactant. In certain embodiments, the solubility enhancing molecule is a cationic surfactant. In certain embodiments, the solubility enhancing molecule has the following structure I:

In certain embodiments, the conjugate is polylysine. In certain embodiments the conjugate comprises diethanolamine molecules linked via a glycolic acid linker. In certain embodiments the conjugate is a small PEG chain.

In certain embodiments, the competitor molecule is added in an amount such that the competitor molecule is present in excess of the oligonucleotide. In certain embodiments, the competitor molecule is added to the test sample in an amount ranging from 50 to 150 pmol. In certain embodiments, the competitor molecule is added to the test sample in an amount ranging from 75 to 125 pmol. In certain embodiments, the competitor molecule is added in an amount ranging from 5 to 15 pmol per 1 ug of RNA. In certain embodiments the competitor molecule is added in an amount ranging from 7 to 12 pmol per 1 ug of RNA.

In certain embodiments, the competitor molecule is added to the test sample in an amount of about 100 pmol. In certain embodiments, the competitor molecule is added at about 10 pmol per 1 ug of RNA. In certain embodiments, the competitor molecule is added in an amount not greater than 500 pmol per gel.

In certain embodiments, the competitor molecule has a neutral or low charge.

In certain embodiments, the oligomeric compound comprises a high affinity modification. In certain embodiments, the oligomeric compound is a peptide nucleic acid. In certain embodiments, the high affinity modification is a sugar modification. In certain embodiments, the high affinity modification is a backbone modification. In certain embodiments, the high affinity modification is a nucleobase modification. In certain embodiments, the oligomeric compound is an oligonucleotide. In certain embodiments, the oligonucleotide comprises one or more high affinity modifications.

In certain embodiments, the oligomeric compound comprises a nucleobase sequence that is at least 90% complementary to the anti-miRNA oligonucleotide. In certain embodiments, the oligomeric compound comprises a nucleobase sequence that is 100% complementary to the anti-miRNA oligonucleotide.

In certain embodiments, free miRNA in the test sample is detected by separating free miRNA from the test sample by electrophoresis in a gel. In certain embodiments, the free miRNA is transferred from the gel to a membrane for detection. In certain embodiments, the membrane is a nylon membrane. In certain embodiments, the miRNA is detected by contacting the membrane with a hybridization probe. In certain embodiments, the hybridization probe is an oligonucleotide having a nucleobase sequence complementary to the nucleobase sequence of the miRNA. In certain embodiments, the hybridization probe is labeled with $^{32}$P-ATP.

In certain embodiments, the anti-miRNA oligonucleotide has a melting temperature of less than 95° C. In certain embodiments, the anti-miRNA oligonucleotide has a melting temperature of less than 90° C. In certain embodiments, the anti-miRNA oligonucleotide has a melting temperature of less than 89° C. In certain embodiments, the anti-miRNA oligonucleotide has a melting temperature of less than 88° C.

In certain embodiments, the anti-miRNA oligonucleotide is at least 80% complementary to the miRNA. In certain embodiments, the anti-miRNA oligonucleotide is at least 85% complementary to the miRNA. In certain embodiments, the anti-miRNA oligonucleotide is at least 90% complementary. In certain embodiments, the anti-miRNA oligonucleotide is at least 95% complementary. In certain embodiments, the anti-miRNA oligonucleotide is 100% complementary to the miRNA. In certain embodiments, one or more nucleosides of the anti-miRNA oligonucleotide comprises a modified sugar. In certain embodiments, each of a plurality of nucleosides of the anti-miRNA oligonucleotide comprises a modified sugar. In certain embodiments, each nucleoside of the anti-miRNA oligonucleotide comprises a modified sugar.

In certain embodiments, a modified sugar is independently selected from a 2'-O-methoxyethyl sugar, a 2'-fluoro sugar, a 2'-O-methyl sugar, or a bicyclic sugar moiety. In certain embodiments, a modified sugar is a 2'-O-methoxyethyl sugar. In certain embodiments, a modified sugar is a bicyclic sugar moiety. In certain embodiments, a modified sugar is a 2'-fluoro sugar. In certain embodiments, a modified sugar is 2'-O-methyl sugar.

In certain embodiments, the anti-miRNA oligonucleotide comprises a plurality of nucleosides having a first modified sugar and a plurality of nucleosides having second modified sugar. In certain embodiments, the first modified sugar is selected from a 2'-O-methoxyethyl sugar, a 2'-fluoro sugar, a 2'-O-methyl sugar, or a bicyclic sugar moiety and the second modified sugar is independently selected from a 2'-O-methoxyethyl sugar, a 2'-fluoro sugar, a 2'-O-methyl sugar, or a bicyclic sugar moiety.

In certain embodiments, each of a plurality of nucleosides of the anti-miRNA oligonucleotide comprises a 2'-O-methoxyethyl sugar and each of a plurality of nucleosides of the anti-miRNA oligonucleotide comprises a 2'-fluoro sugar.

In certain embodiments, at least one internucleoside linkage is a modified internucleoside linkage. In certain embodiments, each internucleoside linkage is a modified internucleoside linkage. In certain embodiments, at least one internucleoside linkage is a phosphorothioate internucleoside linkage. In certain embodiments, each internucleoside linkage is a phosphorothioate internucleoside linkage.

In certain embodiments, an anti-miRNA oligonucleotide is conjugated to cholesterol.

DETAILED DESCRIPTION

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

DEFINITIONS

"Biological sample" means a sample containing nucleic acid. In certain embodiments, the nucleic acid is RNA. In certain embodiments, the RNA is miRNA. In certain embodiments, the biological sample is derived from cells. In certain embodiments, the biological sample is derived from tissues. In certain embodiments, the biological sample is derived from a cell-free system.

"Anti-miRNA oligonucleotide" means an oligonucleotide having a nucleobase sequence that is complementary to the nucleobase sequence of a miRNA.

"Complementary" means a first nucleobase sequence is at least 60%, 65%, 70%, 75%, 80%, 85%, 90%, 95%, 97%, 98% or 99% identical to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions.

"Nucleobase sequence" means the order of contiguous nucleobases, in a 5' to 3' orientation, independent of any sugar, linkage, and/or nucleobase modification.

"Fully complementary" means each nucleobase of a first nucleic acid is capable of pairing with each nucleobase at a corresponding position in a second nucleic acid. For example, in certain embodiments, an oligonucleotide wherein each nucleobase has complementarity to a nucleobase of a miRNA or a precursor thereof has a nucleobase sequence that is identical to the complement of a miRNA or a precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

"Percent complementarity" means the number of complementary nucleobases in a nucleic acid divided by the length of the nucleic acid. In certain embodiments, percent complementarity of an oligonucleotide means the number of nucleobases that are complementary to the target nucleic acid, divided by the length of the modified oligonucleotide.

"Percent identity" means the number of nucleobases in first nucleic acid that are identical to nucleobases at corresponding positions in a second nucleic acid, divided by the total number of nucleobases in the first nucleic acid.

"Substantially identical" used herein may mean that a first and second nucleobase sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Non-complementary nucleobase" means two nucleobases that are not capable of pairing through hydrogen bonding.

"Identical" means having the same nucleobase sequence.

"miRNA" or "miR" means a non-coding RNA between 18 and 25 nucleobases in length, which is the product of cleavage of a pre-miRNA by the enzyme Dicer. Examples of mature miRNAs are found in the miRNA database known as miR-Base (available at the world wide web at microma.sanger.ac.uk).

"Pre-miRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (available at the worldwide web at microma.sanger.ac.uk).

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Oligomeric compound" means a compound comprising a polymer of linked monomeric subunits.

"Oligonucleotide" means a polymer of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Natural nucleobase" means a nucleobase that is unmodified relative to its naturally occurring form.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar.

"Nucleotide" means a nucleoside having a phosphate group covalently linked to the sugar portion of a nucleoside.

"Modified oligonucleotide" means an oligonucleotide having one or more modifications relative to a naturally occurring terminus, sugar, nucleobase, and/or internucleoside linkage.

"Single-stranded modified oligonucleotide" means a modified oligonucleotide which is not hybridized to a complementary strand.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro" or "2'-F" means a sugar having a fluoro modification of the 2' position.

"Bicyclic sugar moiety" means a sugar modified by the bridging of two non-geminal ring atoms.

"2'-O-methoxyethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

"Motif" means a pattern of modified and/or unmodified nucleobases, sugars, and/or internucleoside linkages in an oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Gapmer" means an oligonucleotide having an internal region of linked nucleosides positioned between two external regions of linked nucleosides, where the nucleosides of the internal region comprise a sugar moiety different than that of the nucleosides of each external region.

"Gap segment" is an internal region of a gapmer that is positioned between the external regions.

"Wing segment" is an external region of a gapmer that is located at the 5' or 3' terminus of the internal region.

"Symmetric gapmer" means each nucleoside of each external region comprises the same sugar modification.

"Asymmetric gapmer" means each nucleoside of one external region comprises a first sugar modification, and each nucleoside of the other external region comprises a second sugar modification.

"High affinity modification" means a modification that enhances hybridization between two complementary nucleic acids.

"Stabilizing modification" means a modification to a nucleoside that provides enhanced stability to an oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

"Stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

"Stabilizing internucleoside linkage" means an internucleoside linkage that provides enhanced nuclease stability to an oligonucleotide relative to that provided by a phosphodiester internucleoside linkage. In one embodiment, a stabilizing internucleoside linkage is a phosphorothioate internucleoside linkage.

"Competitor molecule" means a compound capable of hybridizing to an oligonucleotide. In certain embodiments, the oligonucleotide is an anti-miRNA oligonucleotide. In certain embodiments, the compound has a higher affinity for an anti-miRNA oligonucleotide than for the miRNA to which the anti-miRNA oligonucleotide is complementary.

"Solubility enhancing molecule" means a molecule that facilitates the ability of a first substance to dissolve in a second substance. In certain embodiments, the first substance is an oligomeric compound. In certain embodiments, a second substance is an aqueous solution.

"Peptide nucleic acid" means a DNA mimic that incorporates a peptide-like polyamide backbone.

"Hybridization probe" means an oligonucleotide having complementarity to a nucleic acid and containing a detection label. In certain embodiments, the detection label is radioactive adenosine triphosphate (ATP). In certain embodiments the detection label is $^{32}$P-ATP. In certain embodiments, the detection label is digoxigenin.

"Nucleic acid size marker" means a nucleic acid with a known size, which is used to determine the size of an unknown nucleic acid.

Overview

Effective targeting of miRNA has been achieved using anti-miRNA oligonucleotides. These anti-miRNA oligonucleotides comprise various backbone and 2' sugar modifications including 2'-O-methyl (2'-OMe), 2'-O-methoxyethyl (2'-MOE), 2'-fluoro (2° F.), and locked nucleic acid (LNA). Measurement of miRNA levels has been problematic, as measurement of miRNA levels is performed using a hybridization-based method which is subject to interference by the anti-miRNA oligonucleotide. The anti-miRNA oligonucleotide is bound to the miRNA, preventing the hybridization probe from binding to the miRNA and interfering with detection and measurement of the miRNA level. Thus, there is a need for methods to measure miRNA levels in the presence of anti-microRNA oligonucleotides.

Described herein is a method to quantitate miRNA levels in the presence of anti-miRNA oligonucleotide, whereby the miRNA is freed from the anti-miRNA oligonucleotide by adding an excess of a competitor compound that competes for binding to the anti-miRNA oligonucleotide. As demonstrated herein, addition of a competitor molecule to a biological sample results in binding of the competitor molecule to the anti-miRNA oligonucleotide, thereby releasing the anti-miRNA oligonucleotide from the miRNA and making the miRNA available for detection. For example, miRNA in a biological sample was detectable following addition of a peptide nucleic acid competitor molecule to RNA isolated from cells contacted with anti-miRNA oligonucleotide. Accordingly, provided herein are methods for measuring miRNA levels in a biological sample.

Provided herein are methods for measuring small RNA levels in a biological sample. In certain embodiments, the small RNA is a small non-coding RNA. In certain embodiments, the small non-coding RNA is a miRNA.

In certain embodiments, a test sample is prepared from a biological sample. In certain embodiments, the test sample comprises RNA isolated from a biological sample. In certain embodiments, the biological sample is derived from cells. In certain embodiments, the cells are isolated from an animal. In certain embodiments, the biological sample is derived from a tissue. In certain embodiments, the biological sample is derived from a cell-free system. In certain embodiments, the biological sample is derived from cells contacted with an anti-miRNA oligonucleotide. In certain embodiments, the biological sample is derived from tissues contacted with an anti-miRNA olignucleotide. In certain embodiments, the contacting occurs in vitro. In certain embodiments, the contacting occurs in vivo.

In certain embodiments, at least one competitor molecule is added to the test sample. In certain embodiments, the competitor molecule comprises an oligomeric compound. In certain embodiments, the oligomeric compound has a nucleobase sequence complementary to the nucleobase sequence of the anti-miRNA oligonucleotide. In certain embodiments, the oligomeric compound is linked to a conjugate at one terminus. In certain embodiments, the conjugate is at the 5' terminus. In certain embodiments, the conjugate is at the 3' terminus. In certain embodiments, the oligomeric compound comprises a conjugate at each terminus. In certain embodiments, the conjugate is a solubility enhancing molecule. In certain embodiments, the solubility enhancing molecule is a surfactant. In certain embodiments, the solubility enhancing molecule is a cationic surfactant. In certain embodiments, the solubility enhancing molecule has the following structure I:

In certain embodiments, the conjugate is polylysine.

In certain embodiments, the competitor molecule is added in an amount such that the competitor molecule is present in excess of the oligonucleotide. Using routine methods, the amount of the oligonucleotide can be estimated. For example, the amount of oligonucleotide present in a tissue sample from an oligonucleotide-treated animal can be estimated based on the dose of oligonucleotide administered and the accumulation of oligonucleotide in a particular cell type or tissue. A range of competitor molecule concentrations can be tested, to determine the concentration required to free an anti-miRNA oligonucleotide from its target miRNA.

In certain embodiments, the competitor molecule is added to the test sample in an amount ranging from 50 to 150 pmol. In certain embodiments, the competitor molecule is added to the test sample in an amount ranging from 75 to 125 pmol. In certain embodiments, the competitor molecule is added in an amount ranging from 5 to 15 pmol per 1 ug of RNA. In certain embodiments the competitor molecule is added in an amount ranging from 7 to 12 pmol per 1 ug of RNA.

In certain embodiments, the competitor molecule is added to the test sample in an amount of about 100 pmol. In certain embodiments, the competitor molecule is added at about 10 pmol per 1 ug of RNA. In certain embodiments, the competitor molecule is added in an amount not greater than 500 pmol per gel.

In certain embodiments, the competitor molecule has a neutral or low charge. A competitor molecule of neutral or low charge facilitates the electrophoretic separation of the miRNA from the competitor bound to the anti-miRNA oligonucleotide. Such competitor molecules may not enter the gel efficiently, and/or will migrate slower than a free miRNA on a gel, thereby reducing the amount competitor-derived signal during the detection step.

In certain embodiments, the oligomeric compound comprises a high affinity modification. In certain embodiments, the oligomeric compound is a peptide nucleic acid. In certain embodiments, the high affinity modification is a sugar modification. In certain embodiments, the high affinity modification is a backbone modification. In certain embodiments, the high affinity modification is a nucleobase modification. In certain embodiments, the oligomeric compound is an oligonucleotide. In certain embodiments, the oligonucleotide comprises one or more high affinity modifications.

In certain embodiments, the oligomeric compound comprises a nucleobase sequence that is at least 90% complementary to the anti-miRNA oligonucleotide. In certain embodiments, the oligomeric compound comprises a nucleobase sequence that is 100% complementary to the anti-miRNA oligonucleotide.

In certain embodiments, free miRNA in the test sample is detected by separating free miRNA from the test sample by electrophoresis in a gel. In certain embodiments, the free miRNA is transferred from the gel to a membrane for detection. In certain embodiments, the membrane is a nylon membrane. In certain embodiments, the miRNA is detected by contacting the membrane with a hybridization probe. In certain embodiments, the hybridization probe is an oligonucleotide having a nucleobase sequence complementary to the nucleobase sequence of the miRNA. In certain embodiments, the hybridization probe is labeled with $^{32}$P-ATP.

In certain embodiments, free miRNA in the test sample is detected by separating free miRNA from the test sample by capillary electrophoresis. In certain embodiments, the capillary electrophoresis is capillary gel electrophoresis. In certain embodiments the capillary gel electrophoresis uses a polyacrylamide gel. In certain embodiments, the capillary electrophoresis is capillary zone electrophoresis. In certain embodiments, the capillary electrophoresis is performed as described in U.S. Pat. No. 6,045,995, which is herein incorporated by reference in its entirety.

The nucleobase sequence of the competitor molecule shares identity with the nucleobase sequence of the miRNA, and may be detected by the hybridization probe. Thus in certain embodiments, following electrophoresis, the gel is cut to separate the free miRNA containing portion from any excess competitor molecule and/or competitor molecule bound to anti-miRNA oligonucleotide, so that the excess competitor molecule and/or competitor molecule bound to anti-miRNA is not transferred to the membrane. In certain embodiments, a nucleic acid size marker is included when separating the free miRNA from the test sample, to aid in determining which portion of a gel will contain the miRNA.

In certain embodiments, the anti-miRNA oligonucleotide has a melting temperature of less than 95° C. In certain embodiments, the anti-miRNA oligonucleotide has a melting temperature of less than 90° C. In certain embodiments, the anti-miRNA oligonucleotide has a melting temperature of less than 89° C. In certain embodiments, the anti-miRNA oligonucleotide has a melting temperature of less than 88° C.

In certain embodiments, the anti-miRNA oligonucleotide is at least 80% complementary to the miRNA. In certain embodiments, the anti-miRNA oligonucleotide is at least 85% complementary to the miRNA. In certain embodiments, the anti-miRNA oligonucleotide is at least 90% complementary. In certain embodiments, the anti-miRNA oligonucleotide is at least 95% complementary. In certain embodiments, the anti-miRNA oligonucleotide is 100% complementary to the miRNA. In certain embodiments, one or more nucleosides of the anti-miRNA oligonucleotide comprises a modified sugar. In certain embodiments, each of a plurality of nucleosides of the anti-miRNA oligonucleotide comprises a modified sugar. In certain embodiments, each nucleoside of the anti-miRNA oligonucleotide comprises a modified sugar.

In certain embodiments, a modified sugar is independently selected from a 2'-O-methoxyethyl sugar, a 2'-fluoro sugar, a 2'-O-methyl sugar, or a bicyclic sugar moiety. In certain embodiments, a modified sugar is a 2'-O-methoxyethyl sugar.

In certain embodiments, a modified sugar is a bicyclic sugar moiety. In certain embodiments, a modified sugar is a 2'-fluoro sugar. In certain embodiments, a 2'-O-methyl sugar In certain embodiments, the anti-miRNA oligonucleotide comprises a plurality of nucleosides having a first modified sugar and a plurality of nucleosides having second modified sugar. In certain embodiments, the first modified sugar is selected from a 2'-O-methoxyethyl sugar, a 2'-fluoro sugar, a 2'-O-methyl sugar, or a bicyclic sugar moiety and the second modified sugar is independently selected from a 2'-O-methoxyethyl sugar, a 2'-fluoro sugar, a 2'-O-methyl sugar, or a bicyclic sugar moiety.

In certain embodiments, each of a plurality of nucleosides of the anti-miRNA oligonucleotide comprises a 2'-O-methoxyethyl sugar and each of a plurality of nucleosides of the anti-miRNA oligonucleotide comprises a 2'-fluoro sugar.

In certain embodiments, at least one internucleoside linkage is a modified internucleoside linkage. In certain embodiments, each internucleoside linkage is a modified internucleoside linkage. In certain embodiments, at least one internucleoside linkage is a phosphorothioate internucleoside linkage. In certain embodiments, each internucleoside linkage is a phosphorothioate internucleoside linkage.

In certain embodiments, an anti-miRNA oligonucleotide is conjugated to cholesterol.

Certain Compounds

In certain embodiments, an oligonucleotide is conjugated to one or more moieties which enhance the activity, cellular distribution or cellular uptake of the resulting antisense oligonucleotides. In certain embodiments, the moiety allows for detection of the presence of the oligonucleotide in cell, or in a cell-free system. In certain such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to a anti-miRNA oligonucleotide. In certain embodiments, a conjugate group is attached to an oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, a compound comprises an anti-miRNA oligonucleotide having one or more stabilizing groups that are attached to one or both termini of an oligonucleotide to enhance properties such as, for example, nuclease stability. Included in stabilizing groups are cap structures. These terminal modifications protect an oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Nucleobase Sequences

In certain embodiments, an oligonucleotide has a nucleobase sequence that is complementary to a miRNA or a precursor thereof. Nucleobase sequences of mature miRNAs and their corresponding stem-loop sequences described herein are the sequences found in miRBase, an online searchable database of miRNA sequences and annotation, found at the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compositions of the present invention encompass modified oligonucleotides that are complementary any nucleobase sequence version of the miRNAs described herein.

In certain embodiments, a anti-miRNA oligonucleotide has a nucleobase sequence that is complementary to a miRNA or a precursor thereof, meaning that the nucleobase sequence of a anti-miRNA oligonucleotide is a least 60%, 65%, 70%, 75%, 80%, 85%, 90%, 95%, 97%, 98% or 99% identical to the complement of a miRNA or precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. Accordingly, in certain embodiments the nucleobase sequence of a anti-miRNA oligonucleotide may have one or more mismatched basepairs with respect to its target miRNA or precursor sequence, and is capable of hybridizing to its target sequence. In certain embodiments, an anti-miRNA oligonucleotide has a nucleobase sequence that is fully complementary to a miRNA or precursor thereof, meaning that the nucleobase sequence of an anti-miRNA oligonucleotide is 100% identical of the complement of an miRNA or a precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

In certain embodiments, an anti-miRNA oligonucleotide has a sequence that is complementary to a nucleobase sequence of a miRNA stem-loop sequence selected from 1, 2, 3, 4, 5, 6, 7, 8, 9, 10, 11, 12, and 13.

In certain embodiments, an anti-miRNA oligonucleotide has a sequence that is complementary to a nucleobase sequence of a miRNA, where the nucleobase sequence of the miRNA is selected from 14, 15, 16, 17, 18, 19, 20, 21, 22, 23, 24, 25, 26, 27, 28, 29, and 30.

In certain embodiments, an anti-miRNA oligonucleotide has a nucleobase sequence comprising a nucleobase sequence selected from among the nucleobase sequences set forth in 31, 32, 33, 34, 35, 36, 37, 38, 39, 40, 41, 42, 43, 44, 45, 46, and 47.

In certain embodiments, an anti-miRNA oligonucleotide has a nucleobase sequence consisting of a nucleobase sequence selected from among the nucleobase sequences set forth in 31, 32, 33, 34, 35, 36, 37, 38, 39, 40, 41, 42, 43, 44, 45, 46, and 47.

In certain embodiments, an anti-miRNA oligonucleotide has a nucleobase sequence that is complementary to a nucleobase sequence of a pri-miR sequence comprising a mature miRNA selected from 14, 15, 16, 17, 18, 19, 20, 21, 22, 23, 24, 25, 26, 27, 28, 29, and 30.

In certain embodiments, an anti-miRNA oligonucleotide has a nucleobase sequence that is complementary to a nucleobase sequence having at least 80% identity to a nucleobase sequence of a miRNA stem-loop sequence selected from 1, 2, 3, 4, 5, 6, 7, 8, 9, 10, 11, 12, and 13. In certain embodiments, an anti-miRNA oligonucleotide has a nucleobase sequence that is complementary to a nucleobase sequence having at least 85%, at least 90%, at least 92%, at least 94%, at least 96%, or at least 98% identity to a nucleobase sequence of a miRNA stem-loop sequence selected from 1, 2, 3, 4, 5, 6, 7, 8, 9, 10, 11, 12, and 13.

In certain embodiments, an anti-miRNA oligonucleotide has a nucleobase sequence that is complementary to a nucleobase sequence having at least 80% identity to a nucleobase sequence of a miRNA having a nucleobase sequence selected from 14, 15, 16, 17, 18, 19, 20, 21, 22, 23, 24, 25, 26, 27, 28, 29, and 30. In certain embodiments, an anti-miRNA oligonucleotide has a nucleobase sequence that is complementary to a nucleobase sequence having at least 85%, at least 90%, at least 92%, at least 94%, at least 96%, or at least 98% identity to a nucleobase sequence of a miRNA nucleobase sequence selected from 14, 15, 16, 17, 18, 19, 20, 21, 22, 23, 24, 25, 26, 27, 28, 29, and 30.

In certain embodiments, a nucleobase sequence of an anti-miRNA oligonucleotide is fully complementary to a miRNA nucleobase sequence listed herein, or a precursor thereof. In certain embodiments, an anti-miRNA oligonucleotide has a nucleobase sequence having one mismatch with respect to the nucleobase sequence of the mature miRNA, or a precursor thereof. In certain embodiments, an anti-miRNA oligonucleotide has a nucleobase sequence having two mismatches with respect to the nucleobase sequence of the miRNA, or a precursor thereof. In certain such embodiments, an anti-miRNA oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, an anti-miRNA oligonucleotide consists of a number of linked nucleosides that is equal to the length of the mature miRNA to which it is complementary.

In certain embodiments, the number of linked nucleosides of an anti-miRNA oligonucleotide is less than the length of the mature miRNA to which it is complementary. In certain such embodiments, the number of linked nucleosides of an anti-miRNA oligonucleotide is one less than the length of the mature miRNA to which it is complementary. In certain such embodiments, an anti-miRNA oligonucleotide has one less nucleoside at the 5' terminus. In certain such embodiments, an anti-miRNA oligonucleotide has one less nucleoside at the 3' terminus. In certain such embodiments, an anti-miRNA oligonucleotide has two fewer nucleosides at the 5' terminus. In certain such embodiments, an anti-miRNA oligonucleotide has two fewer nucleosides at the 3' terminus. An anti-miRNA oligonucleotide having a number of linked nucleosides that is less than the length of the miRNA, wherein each nucleobase of an anti-miRNA oligonucleotide is complementary to each nucleobase at a corresponding position in a miRNA, is considered to be an anti-miRNA oligonucleotide having a nucleobase sequence that is fully complementary to a portion of a miRNA sequence.

In certain embodiments, the number of linked nucleosides of an anti-miRNA oligonucleotide is greater than the length of the miRNA to which it is complementary. In certain such embodiments, the nucleobase of an additional nucleoside is complementary to a nucleobase of a miRNA stem-loop sequence. In certain embodiments, the number of linked nucleosides of an anti-miRNA oligonucleotide is one greater than the length of the miRNA to which it is complementary. In certain such embodiments, the additional nucleoside is at the 5' terminus of an anti-miRNA oligonucleotide. In certain such embodiments, the additional nucleoside is at the 3' terminus of an anti-miRNA oligonucleotide. In certain embodiments, the number of linked nucleosides of an anti-miRNA oligonucleotide is two greater than the length of the miRNA to which it is complementary. In certain such embodiments, the two additional nucleosides are at the 5' terminus of an anti-miRNA oligonucleotide. In certain such embodiments, the two additional nucleosides are at the 3' terminus of an anti-miRNA oligonucleotide. In certain such embodiments, one additional nucleoside is located at the 5' terminus and one additional nucleoside is located at the 3' terminus of an anti-miRNA oligonucleotide.

In certain embodiments, a portion of the nucleobase sequence of an anti-miRNA oligonucleotide is fully complementary to the nucleobase sequence of the miRNA, but the entire modified oligonucleotide is not fully complementary to the miRNA. In certain such embodiments, the number of nucleosides of an anti-miRNA oligonucleotide having a fully complementary portion is greater than the length of the miRNA. For example, an anti-miRNA oligonucleotide consisting of 24 linked nucleosides, where the nucleobases of nucleosides 1 through 23 are each complementary to a corresponding position of a miRNA that is 23 nucleobases in length, has a 23 nucleoside portion that is fully complementary to the nucleobase sequence of the miRNA and approximately 96% overall complementarity to the nucleobase sequence of the miRNA.

In certain embodiments, the nucleobase sequence of an anti-miRNA oligonucleotide is fully complementary to a portion of the nucleobase sequence of a miRNA. For example, an anti-miRNA oligonucleotide consisting of 22 linked nucleosides, where the nucleobases of nucleosides 1 through 22 are each complementary to a corresponding position of a miRNA that is 23 nucleobases in length, is fully complementary to a 22 nucleobase portion of the nucleobase sequence of a miRNA. Such an anti-miRNA oligonucleotide has approximately 96% overall complementarity to the nucleobase sequence of the entire miRNA, and has 100% complementarity to a 22 nucleobase portion of the miRNA.

In certain embodiments, a portion of the nucleobase sequence of an anti-miRNA oligonucleotide is fully complementary to a portion of the nucleobase sequence of a miRNA, or a precursor thereof. In certain such embodiments, 15 contiguous nucleobases of an anti-miRNA oligonucleotide are each complementary to 15 contiguous nucleobases of a miRNA, or a precursor thereof. In certain such embodiments, 16 contiguous nucleobases of an anti-miRNA oligonucleotide are each complementary to 16 contiguous nucleobases of a miRNA, or a precursor thereof. In certain such embodiments, 17 contiguous nucleobases of an anti-miRNA oligonucleotide are each complementary to 17 contiguous nucleobases of a miRNA, or a precursor thereof. In certain such embodiments, 18 contiguous nucleobases of an anti-miRNA oligonucleotide are each complementary to 18 contiguous nucleobases of a miRNA, or a precursor thereof. In certain such embodiments, 19 contiguous nucleobases of an anti-miRNA oligonucleotide are each complementary to 19 contiguous nucleobases of a miRNA, or a precursor thereof. In certain such embodiments, 20 contiguous nucleobases of an anti-miRNA oligonucleotide are each complementary to 20 contiguous nucleobases of a miRNA, or a precursor thereof. In certain such embodiments, 22 contiguous nucleobases of an anti-miRNA oligonucleotide are each complementary to 22 contiguous nucleobases of a miRNA, or a precursor thereof. In certain such embodiments, 23 contiguous nucleobases of an anti-miRNA oligonucleotide are each complementary to 23 contiguous nucleobases of a miRNA, or a precursor thereof. In certain such embodiments, 24 contiguous nucleobases of an anti-miRNA oligonucleotide are each complementary to 24 contiguous nucleobases of a miRNA, or a precursor thereof.

Certain Modified Oligonucleotides

In certain embodiments, an oligonucleotide consists of 15 to 30 linked nucleosides. In certain embodiments, an oligonucleotide consists of 19 to 24 linked nucleosides. In certain embodiments, an oligonucleotide consists of 21 to 24 linked nucleosides. In certain embodiments, an oligonucleotide consists of 15 linked nucleosides. In certain embodiments, an oligonucleotide consists of 16 linked nucleosides. In certain embodiments, an oligonucleotide consists of 17 linked nucleosides. In certain embodiments, an oligonucleotide consists of 18 linked nucleosides. In certain embodiments, an oligonucleotide consists of 19 linked nucleosides. In certain embodiments, an oligonucleotide consists of 20 linked nucleosides. In certain embodiments, an oligonucleotide consists of 21 linked nucleosides. In certain embodiments, an oligonucleotide consists of 22 linked nucleosides. In certain embodiments, an oligonucleotide consists of 23 linked nucleosides. In certain embodiments, an oligonucleotide consists of 24 linked nucleosides. In certain embodiments, an oligonucleotide consists of 25 linked nucleosides. In certain embodiments, an oligonucleotide consists of 26 linked nucleosides. In certain embodiments, an oligonucleotide consists of 27 linked nucleosides. In certain embodiments, an oligonucleotide consists of 28 linked nucleosides. In certain embodiments, an oligonucleotide consists of 29 linked nucleosides. In certain embodiments, an oligonucleotide consists of 30 linked nucleosides.

Certain Modifications

An oligonucleotide may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, an oligonucleotide comprises one or more modified nucleosides. In certain embodiments, a modified nucleoside is a stabilizing nucleoside. An example of a stabilizing nucleoside is a sugar-modified nucleoside.

In certain embodiments, a modified nucleoside is a sugar-modified nucleoside. In certain embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)$_2$—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—(CH$_2$)$_p$—, —O—CH$_2$—, —O—CH$_2$CH$_2$—, —O—CH(alkyl)-, —NH—(CH$_2$)$_p$—, —N(alkyl)-(CH$_2$)$_p$—, —O—CH(alkyl)-, —(CH(alkyl))—(CH$_2$)$_p$—, —NH—O—(CH$_2$)$_p$—, —N(alkyl)-O—(CH$_2$)$_p$—, or —O—N(alkyl)-(CH$_2$)$_p$—, wherein p is 1, 2, 3, 4 or 5 and each alkyl group can be further substituted. In certain embodiments, p is 1, 2 or 3.

In certain embodiments, a 2'-modified nucleoside comprises a 2'-substituent group selected from halo, allyl, amino, azido, SH, CN, OCN, CF$_3$, OCF$_3$, O—, S—, or N($R_m$)-alkyl; O—, S—, or N($R_m$)-alkenyl; O—, S— or N($R_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N($R_m$)($R_n$) or O—CH$_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, $O—CH_3$, $O(CH_2)_3NH_2$, $CH_2—CH=CH_2$, $O—CH_2—CH=CH_2$, $OCH_2CH_2OCH_3$, $O(CH_2)_2SCH_3$, $O—(CH_2)_2—O—N(R_m)(R_n)$, $—O(CH_2)_2—O—(CH_2)_2N(CH_3)_2$, and N-substituted acetamide $(O—CH_2—C(=O)—N(R_m)(R_n)$ where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, $O—CH_3$, $OCH_2CH_2OCH_3$, 2'-$O(CH_2)_2SCH_3$, $O—(CH_2)_2—O—N(CH_3)_2$, $—O(CH_2)_2—O—(CH_2)_2N(CH_3)_2$, and $O—CH_2—C(=O)—N(H)CH_3$.

In certain embodiments, a 2'-modified nucleoside comprises a 2'-substituent group selected from F, $O—CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-$O—(CH_2)_2—OCH_3$, and 2'-F.

In certain embodiments, an oligonucleotide comprises one or more internucleoside modifications. In certain such embodiments, each internucleoside linkage of an anti-miRNA oligonucleotide is a modified internucleoside linkage. In certain embodiments, a modified internucleoside linkage comprises a phosphorus atom.

In certain embodiments, an oligonucleotide comprises at least one phosphorothioate internucleoside linkage. In certain embodiments, each internucleoside linkage of an anti-miRNA oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and $CH_2$ component parts.

In certain embodiments, an oligonucleotide comprises one or more modified nucleobases. In certain embodiments, an oligonucleotide comprises one or more 5-methylcytosines. In certain embodiments, each cytosine of an oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and $N^2$, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Oligonucleotide Motifs

Suitable motifs for oligonucleotides include, but are not limited to, fully modified, uniformly modified, positionally modified, and gapmer. Oligonucleotides having a fully modified motif, including a uniformly modified motif, may have a nucleobase sequence complementary to the nucleobase sequence of a miRNA. Alternatively, oligonucleotides having a fully modified motif, including a uniformly modified motif, may be designed to target certain sites of pri-miRNAs or pre-miRNAs, to block the processing of miRNA precursors into mature miRNAs. Oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O-methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain such embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of an oligonucleotide comprises a 2'-O-methoxyethyl sugar modification. In certain embodiments, each nucleoside of an oligonucleotide comprises a 2'-O-methyl sugar modification. In certain embodiments, each nucleoside of an oligonucleotide comprises a 2'-fluoro sugar modification. In certain such embodiments, a uniformly modified oligonucleotide further comprises at least one modified internucleoside linkage. In certain such embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleotide comprises the same internucleoside linkage modifications throughout. In certain such embodiments, each internucleoside linkage of a uniformly modified oligonucleotide is a phosphorothioate internucleoside linkage.

In certain embodiments, an oligonucleotide comprises the same sugar modification at each nucleoside, and further comprises one or more internucleoside linkage modifications. In certain such embodiments, the modified oligonucleotide comprises one modified internucleoside linkage at the 5' terminus and one modified internucleoside linkage at the 3' terminus. In certain embodiments, the modified oligonucleotide comprises two modified internucleoside linkages at the 5' terminus and two modified internucleoside linkages at the 3' terminus. In certain embodiments, the modified oligonucleotide comprises two modified internucleoside linkages at the 5' terminus and three modified internucleoside linkages at the 3' terminus. In certain embodiments, the modified oligonucleotide comprises two modified internucleoside linkages at the 5' terminus and four modified internucleoside linkages at the 3' terminus. In certain such embodiments, the modified internucleoside linkage is a phosphorothioate internucleoside linkage.

Certain Assays

The effects of antisense inhibition of a miRNA following the administration of modified oligonucleotides may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan® MicroRNA Assay (Applied Biosystems). In certain embodiments, antisense inhibition of a miRNA is assessed by measuring the mRNA and/or protein level of a target of a miRNA. Antisense inhibition of a miRNA generally results in the increase in the level of mRNA and/or protein of a target of the miRNA.

Kits

In some embodiments, the present invention provide kits for performing the methods described herein. The kits can, for example, comprise instructions for detecting miRNA in a biological sample. The instructions can include methods for detecting the free miRNA by separation free miRNA from the test sample by electrophoresis in a gel. The kit can also comprise components for performing the methods described herein. The kit can also comprise instructions for a method comprising contacting a cell with an anti-miRNA oligonucleotide; isolating RNA from the cell to form a biological sample; preparing a test sample comprising the biological sample; adding at least one competitor molecule to the test sample; detecting free miRNA in the test sample, thereby detecting the miRNA amount in the biological sample.

The kit can include, for example, at least one competitor molecule, at least one positive control, or at least one negative control. The kit can comprises at least one competitor molecule in a sufficient amount such that it can be added to a test sample in an amount from 50 to 150 pmol. The kit can comprise at least one competitor molecule in a sufficient amount to be added to the test sample in an amount from 5 to 15 pmol per 1 µg of RNA. In some embodiments, the kit comprises a competitor molecule that comprises an oligomeric compound having a nucleobase sequence complementary to the nucleobase sequence of an anti-miRNA oligonucleotide. In some embodiments, the oligomeric compound comprises a conjugate at least one terminus. The kit can comprise a competitor molecule that comprises an oligomeric compound comprising a conjugate at least one terminus, wherein the conjugate is a solubility enhancing molecule. In some embodiments, the solubility enhancing molecule has the structure of Structure.

The kit can comprise the oligomeric compound wherein the oligomeric compound comprises at least one high affinity modification. The oligomeric compound can also comprise at least one peptide nucleic acid modification. In some embodiments, the kit comprises an oligomeric compound that comprises a nucleobase sequence that is at least 90% complementary to the anti-miRNA oligonucleotide. The oligomeric compound can also comprise a nucleobase sequence that is 100% complementary to the anti-miRNA oligonucleotide.

The kit can also comprise an anti-mRNA oligonucleotide. In some embodiments, one or more nucleosides of the anti-miRNA oligonucleotide comprises at least one modified sugar. In some embodiments, each of a plurality of nucleosides of the anti-miRNA oligonucleotide comprises a modified sugar. In some embodiments, the kit comprises an anti-mRNA, wherein each nucleoside of the anti-miRNA oligonucleotide comprises a modified sugar. The kit can also comprise an anti-miRNA oligonucleotide is conjugated to cholesterol.

The following examples are presented in order to more fully illustrate some embodiments of the invention. They should, in no way be construed, however, as limiting the broad scope of the invention.

EXAMPLES

Example 1

Assay for miRNA Detection

Oligonucleotides are used to inhibit the activity of a target nucleic acid in in vitro and in vivo assays. Following treatment of a cell, tissue or animal with an oligonucleotide, the amount of the target nucleic acid is often measured. A technique for such measurements includes the hybridization-based northern blot. In the case of microRNAs, which are about 20-23 nucleobases in length, an anti-miRNA oligonucleotide that is bound to its target microRNA can interfere with detection by northn blot. Described herein is an assay that was developed to circumvent this interference problem and permit detection of microRNA amounts in a sample treated with anti-miRNA oligonucleotides. This assay can be used for anti-miRNA oligonucleotides having a variety of chemical modifications or melting temperatures.

Figure 2:
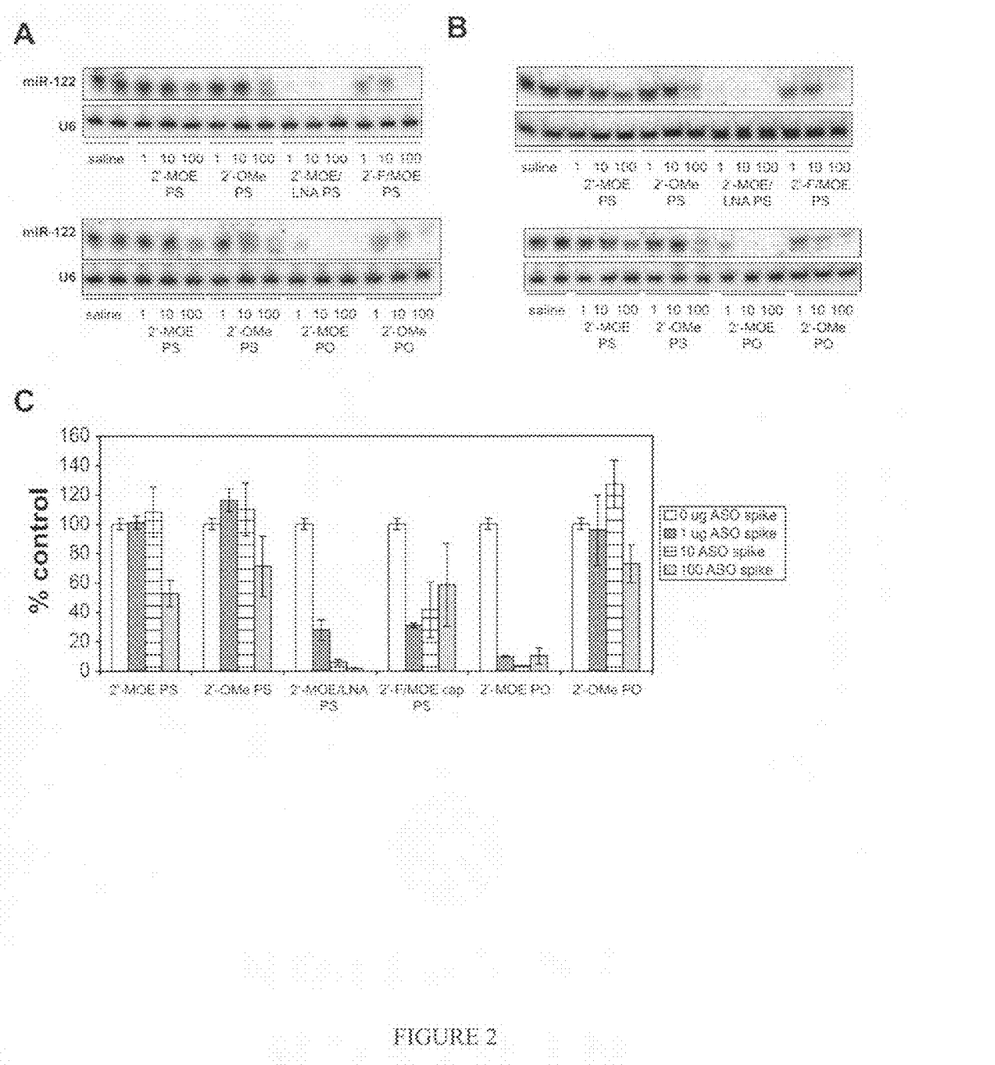
Figure 3:
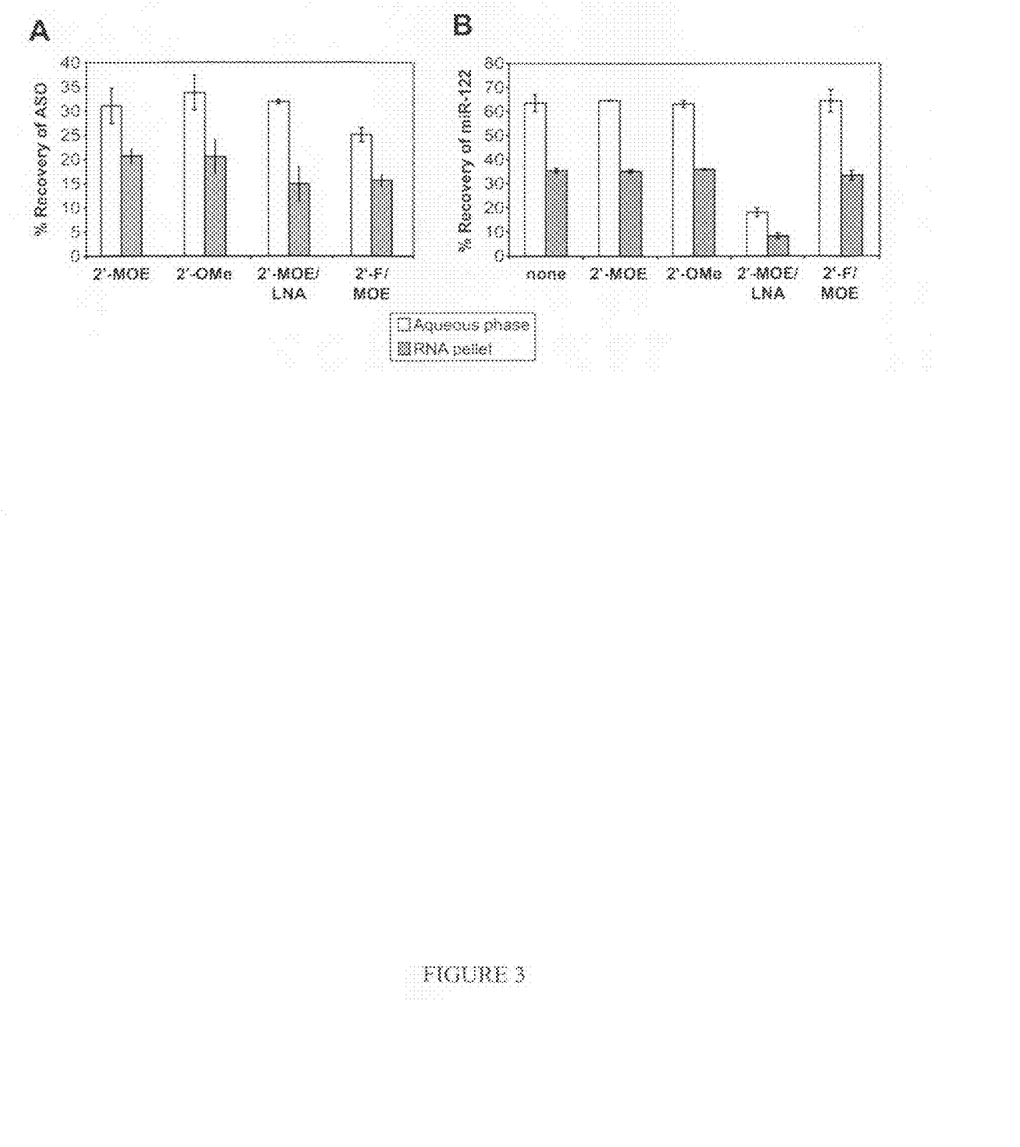
FIG. 3 Recovery of ASOs and miR-122 in presence of ASOs through Trizol purification process. (a) Recovery of radiolabeled ASOs after Trizol purification of liver RNA. (b) Recovery of radiolabeled miR-122 in presence of ASOs after Trizol purification of liver RNA.
Figure 4:
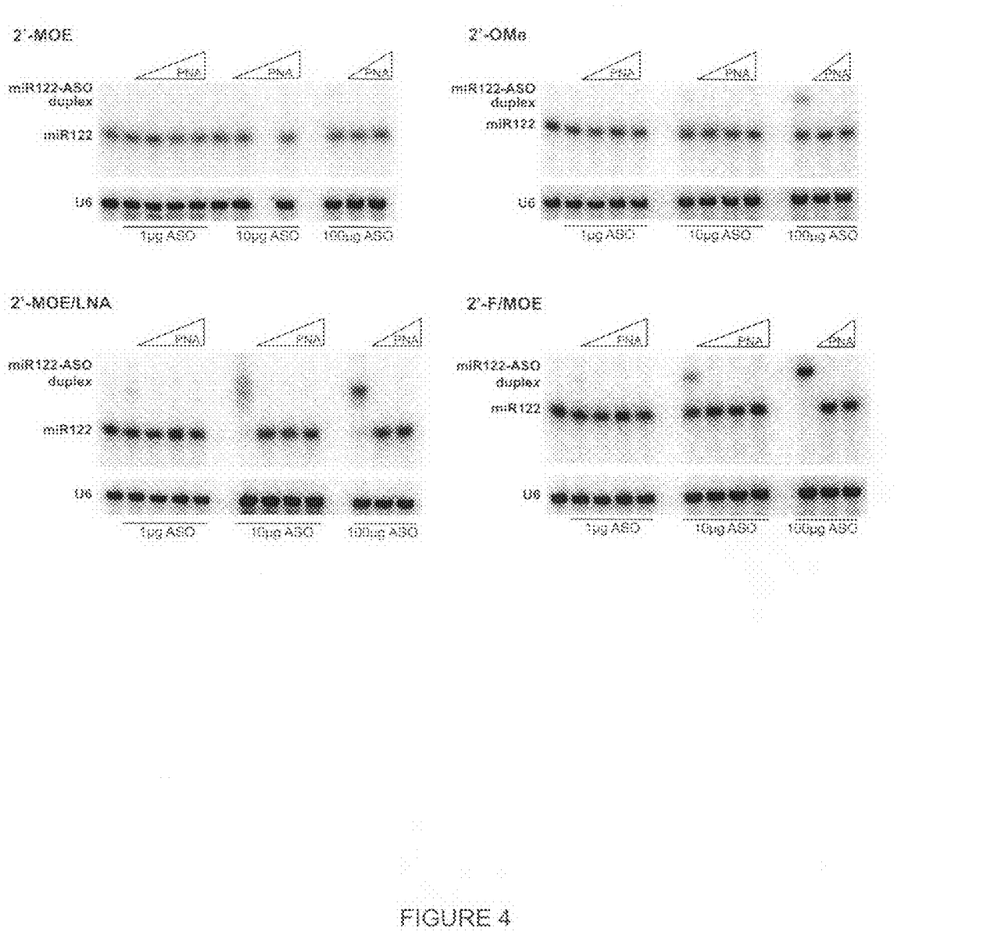
FIG. 4 PNA competitor molecule has ability to free miR-122 from miR122-ASO duplex in mouse total liver RNA. The indicated ASOs were added to liver lysates and RNA was Trizol-purified. Radiolabeled miR-122 RNA was added to RNA sample, RNA was separated by denaturing PAGE in presence of PNA competitor molecule and transferred to membrane, which was exposed on a phosphoimager. Northern blotting for U6 was also performed for normalization.
Figure 5:
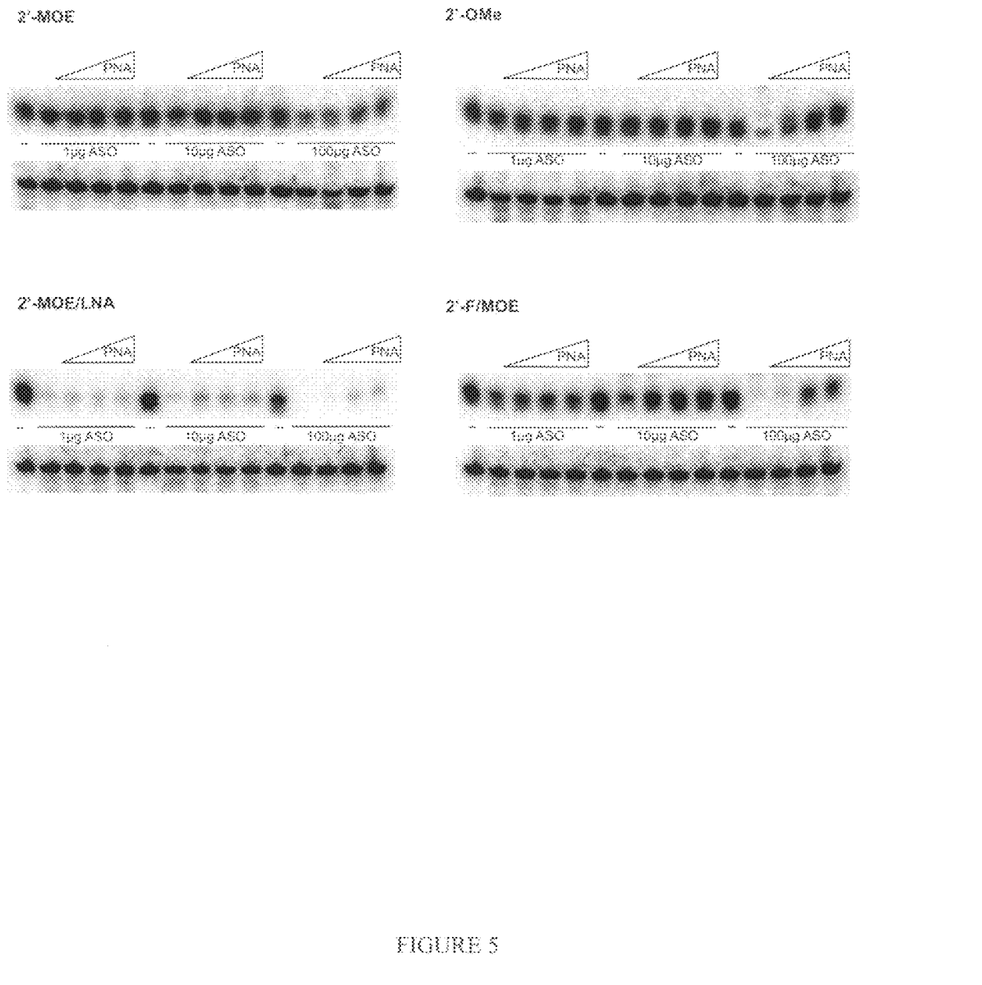
FIG. 5. PNA competitor molecule restores northern detection of miR-122 in the presence of anti-miRNA ASOs. The indicated ASOs were added to liver lysates and RNA was Trizol-purified. RNA was separated by denaturing PAGE in presence of PNA competitor molecule and northern blotting for miR-122 was performed.

The degree of interference observed on a northern blot may be largely related to the affinity of an anti-miRNA oligonucleotide for an miRNA. However, an anti-miRNA oligonucleotide comprising 2'-fluoro and 2'-MOE modification, which has a similar $T_m$ as a uniformly 2'-MOE modified anti-miRNA oligonucleotide, nevertheless showed significantly greater interference with detection of miR-122. One possibility is that there are differences in the recovery of the anti-miRNA oligonucleotides during the RNA purification process which would lead to different degrees of interference with miR-122 detection during northern blotting. To investigate this, anti-miRNA oligonucleotides were labeled at the 5' end with $^{32}P$, and equivalent cpms were added to Trizol lysates of mouse liver tissue. RNA was subsequently purified. Tracking the radiolabeled anti-miRNA oligonucleotides through the preparations showed that all anti-miRNA oligonucleotides were similarly recovered through the RNA preparation process (FIG. 2a). Therefore, it was unlikely that differential anti-miRNA oligonucleotide recovery accounted for the different degrees of interference by the anti-miRNA oligonucleotides.

While a large portion of the anti-miRNA oligonucleotides persist through the RNA preparation process, the majority of anti-miRNA oligonucleotide remains in the organic phase. Some anti-miRNA oligonucleotides may remain bound to the miRNA during the Trizol purification, partitioning the miRNA into the organic phase during the phase separation step of the RNA isolation, resulting in artifactual reductions in miRNA levels. To evaluate this, miR-122 RNA was labeled with $^{32}P$ and added, together with unlabeled anti-miRNA oligonucleotide, to Trizol lysates of liver tissue. RNA was purified and recovery of labeled miR-122 was assessed (FIG. 2b). Overall recovery of the miRNA in the presence of the high affinity anti-miRNA oligonucleotide comprising 2'-MOE and LNA sugar modifications was four-fold reduced compared to the other anti-miRNA oligonucleotides, none of which had any significant effect on miR-122 recovery. The percent recovery of miR-122 during the precipitation step was similar for all the anti-miRNA oligonucleotides, indicating that the miRNA is primarily lost during the initial phase separation. Other high affinity anti-miRNA oligonucleotides similarly retained the miRNA in the organic phase.

Figure 1:
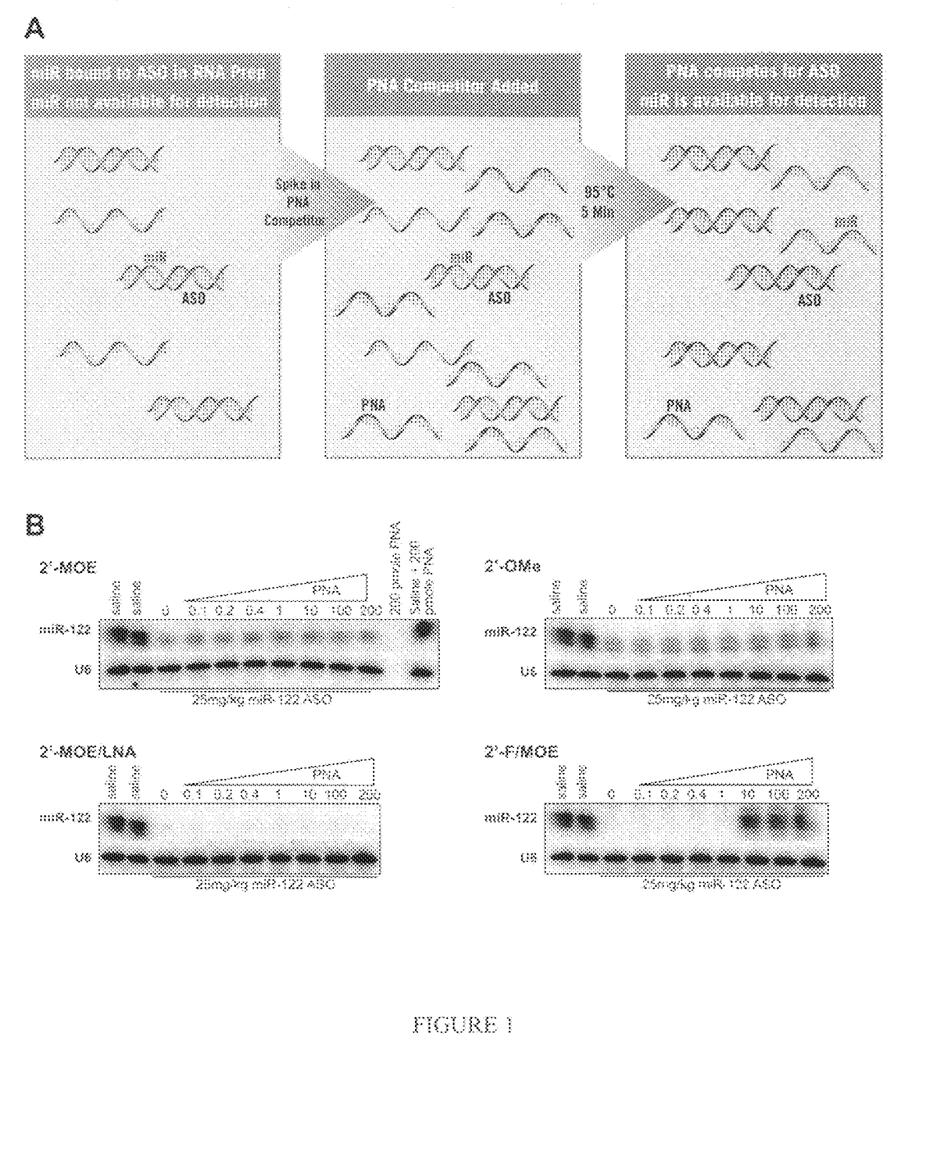
FIG. 1 Quantitation of miR-122 levels after in vivo inhibition with anti-miR-122 ASOs. Normal mice were treated i.p. with 25 mg/kg dose of miR-122 ASOs twice weekly for three weeks. n=5 (a) PNA competitor molecule strategy to recover detection of microRNAs in the presence of anti-miRNA oligonucleotide. (b) Northern blotting for miR-122 after separation of RNA by denaturing PAGE in presence of PNA competitor molecule.

Thus, with the exception of the anti-miRNA oligonucleotide comprising 2'-MOE and LNA sugar modifications, the RNA purification does not contribute to anti-miRNA oligonucleotide interference with miRNA detection. In order to more accurately quantify miRNA levels in the presence of anti-miRNA oligonucleotides, a strategy was devised to free the miRNA from the anti-miRNA oligonucleotide after RNA purification by adding an excess of high affinity peptide nucleic acid (PNA) complementary to the anti-miRNA oligonucleotide to compete for its binding, thereby making it available for northern hybridization (FIG. 1a). When the RNA sample containing both anti-miRNA oligonucleotide and PNA is separated on a polyacrylamide gel by electrophoresis, the anti-miRNA oligonucleotide is bound by PNA and shifted on the gel, preventing any interference with probe hybridization with the miRNA. Moreover, any unbound PNA, due to its neutral charge, will not travel into the gel, thus preventing detection of the PNA by the hybridization probe, which would interfere with detection of the miRNA.

The feasability of the PNA competitor molecule approach was shown by its ability to free radiolabeled miR-122 from a miRNA-anti-miRNA oligonucleotide duplex (FIG. 1). The PNA competitor molecule's ability to restore northern detection of miR-122 in the presence of anti-miRNA oligonucleotide was evaluated. 1, 10 or 100 µg of anti-miRNA oligonucleotide was added into Trizol lysates containing 50 mg mouse liver tissue. PNA competitor molecule was added to the samples, which were then separated on a denaturing gel, blotted, and probed for miR-122. Under conditions in which the uniformly 2'-MOE modified and uniformly 2'-OMethyl modified anti-miRNA oligonucleotides interfered with miRNA detection, the PNA competitor molecule permitted detection of miR-122. The PNA competitor molecule also restored the miR-122 signal in the presence of 1 and 10 µg of the anti-miRNA oligonucleotide comprising 2'-fluoro and 2'-MOE modifications. Restoration of the miR-122 signal in the samples containing 100 µg of the anti-miRNA oligonucleotide comprised of 2'-fluoro and 2'-MOE modifications. The PNA competitor molecule's inability to restore the miR-122 signal in the presence of the anti-miRNA oligonucleotide comprised of 2'-MOE and LNA modification was not surprising, since miR-122 is retained by this anti-miRNA oligonucleotide in the organic phase during RNA purification and is therefore not present to be recovered.

Example 2 miR-122 Levels After in Vivo Administration of Anti-miRNA Oligonucleotide

The assay described herein was used this assay to evaluate the effect of in vivo anti-miRNA oligonucleotide inhibition on miR-122 levels. PNA competitor molecule was added to mouse liver RNA from the study described in FIG. 1, and northern blotting for miR-122 was performed. The tissue levels of the uniformly modified 2'-MOE and uniformly modified 2'-OMe anti-miRNA oligonucleotide after this three week dosing regimen are not expected to be in a range where interference with miRNA detection is likely. Without any PNA competitor molecule, a five-fold reduction in miRNA levels was measured, and addition of PNA competitor molecule did not recover any further signal. Similar results were obtained for the 2'-OMe oligonucleotide, which also caused a five-fold reduction in miR-122 levels. No miR-122 signal was recovered in the sample from a mouse treated with anti-miRNA oligonucleotide comprised of 2'-MOE and LNA modifications, as expected. Finally, while miR-122 detection in the RNA from mice treated with anti-miRNA oligonucleotide comprised of 2'-fluoro and 2'-MOE was completely inhibited, 80% of the miRNA signal could be restored by addition of the PNA competitor molecule.

Example 3

Northern Blotting

Total RNA was purified using Trizol reagent (Invitrogen). 10 µg total RNA in 1×TBE-Urea loading buffer (Invitrogen) was separated on a 15% TBE-Urea polyacrylamide gel (Invitrogen) or a 14% TBE-Urea polyacrylamide gel with 20% formamide. Samples run on formamide containing gels were also loaded in 20% formamide. RNA was transferred to Hybond N+ membranes (Amersham) at 30V for 2 hours and UV cross-linked. Blots were pre-hybridized in Rapid-Hyb Buffer (GE Healthcare) for 1 hour at 42° C., then hybridized with a $^{32}P$ end-labeled DNA probe for 4 hours at 42° C. Blots were washed in 5×SSC buffer+0.1% SDS twice for five minutes at room temperature and exposed overnight. Quantitation was done using a Storm 860 phosphoimager (Molecular Dynamics) and ImageQuant software.

Example 4

PNA Competition Assay

PNA competitor molecule was obtained from Panagene. PNA competitor molecule was added to 10 µg total RNA in 1×TBE-Urea loading buffer (Invitrogen). Samples were mixed and heated at 95° C. for 3 minutes prior to loading on 15% TBE-Urea polyacrylamide gel (Invitrogen). Prior to electroblotting, the top portion of the gel containing excess PNA competitor molecule was cut and separated from lower miRNA-containing portion. Use of a 23 bp fluoroscein-labeled oligonucleotide aided in gel separation. After electroblotting, UV crosslinking, and prehybridization as described, the prehybridization buffer was exchanged for fresh buffer and blots were then hybridized for 4 hours at 42° C. Blots were washed in 5×SSC buffer+0.1% SDS (Invitrogen) twice for five minutes and exposed overnight.

What is claimed:

1. A method comprising:
    contacting a cell with an anti-miRNA oligonucleotide;
    isolating RNA from the cell to form a biological sample;
    preparing a test sample comprising the biological sample;
    adding at least one competitor molecule to the test sample, wherein the competitor molecule comprises an oligomeric compound comprising a nucleobase sequence that is at least 90% complementary to the nucleobase sequence of the anti-miRNA oligonucleotide; and
    detecting free miRNA in the test sample, thereby detecting the miRNA amount in the biological sample.

2. The method of claim 1, wherein the free miRNA is detected by separating free miRNA from the test sample by gel electrophoresis.

3. The method of claim 1, wherein the anti-miRNA oligonucleotide has a melting temperature of less than 95° C.

4. The method of claim 1, wherein the competitor molecule is added to the test sample in an amount from 50 to 150 pmol.

5. The method of claim 1, wherein the competitor molecule is added in an amount from 5 to 15 pmol per 1 ug of RNA.

6. The method of claim 1, wherein the competitor molecule is added in an amount not greater than 500 pmol per gel.

7. The method of claim 6, wherein the oligomeric compound comprises a conjugate at least one terminus.

8. The method of claim 7, wherein the conjugate is a solubility enhancing molecule.

9. The method of claim 8, wherein the solubility enhancing molecule has the following Structure I:

Structure I

10. The method of claim 1, wherein the oligomeric compound comprises at least one high affinity modification.

11. The method of claim 1, wherein the oligomeric compound comprises at least one peptide nucleic acid modification.

12. The method of claim 1, wherein the oligomeric compound comprises a nucleobase sequence that is 100% complementary to the anti-miRNA oligonucleotide.

13. The method of claim 1, wherein one or more nucleosides of the anti-miRNA oligonucleotide comprises at least one modified sugar.

14. The method of claim 1, wherein each of a plurality of nucleosides of the anti-miRNA oligonucleotide comprises a modified sugar.

15. The method of claim 1, wherein each nucleoside of the anti-miRNA oligonucleotide comprises a modified sugar.

16. The method of claim 1, wherein the anti-miRNA oligonucleotide is conjugated to cholesterol.

* * * * *